(12) United States Patent
Pinney

(10) Patent No.: US 6,242,489 B1
(45) Date of Patent: Jun. 5, 2001

(54) MALODORANT COMPOSITIONS

(75) Inventor: Virginia Ruth Pinney, The Woodlands, TX (US)

(73) Assignee: Ecological Technologies Corporation, The Woodlands, TX (US)

( * ) Notice: Subject to any disclaimer, the term of this patent is extended or adjusted under 35 U.S.C. 154(b) by 0 days.

(21) Appl. No.: 09/257,913

(22) Filed: Mar. 2, 1999

Related U.S. Application Data

(63) Continuation-in-part of application No. 09/088,334, filed on Jun. 1, 1998, now abandoned, which is a continuation-in-part of application No. 08/937,909, filed on Sep. 25, 1997, now abandoned.

(51) Int. Cl.[7] ................................................ A01N 37/14
(52) U.S. Cl. ............................................ 514/562; 514/957
(58) Field of Search ...................................... 514/562, 957

(56) References Cited

U.S. PATENT DOCUMENTS

| | | |
|---|---|---|
| 1,643,954 | 10/1927 | Prentice . |
| 2,159,241 | 5/1939 | Williams ................................ 167/47 |
| 3,402,665 | 9/1968 | Tarpley, Jr. et al. .................... 102/65 |
| 3,528,662 | 9/1970 | Merchant et al. ................. 273/106.5 |
| 3,752,659 | 8/1973 | Crouch et al. ................... 48/197 FM |
| 3,861,350 | 1/1975 | Selleck ................................. 116/114 |
| 4,275,820 | * 6/1981 | LeBlond .................................... 223/3 |
| 4,487,613 | 12/1984 | Yoshida et al. ................. 48/197 FM |
| 5,001,880 | 3/1991 | Smith ..................................... 53/453 |
| 5,161,680 | * 11/1992 | Badgley ................................ 206/38 |
| 5,254,379 | 10/1993 | Kotsiopoulos et al. ............. 428/35.7 |
| 5,405,599 | 4/1995 | Porrovecchio ........................... 424/2 |
| 5,639,526 | 6/1997 | Kotsiopoulos et al. ............. 473/577 |
| 5,821,450 | 10/1998 | Fedida ................................. 102/370 |

FOREIGN PATENT DOCUMENTS

| | | |
|---|---|---|
| 0002879 | 7/1979 | (EP) . |
| 0758634 | 2/1997 | (EP) . |
| 9965847 | * 12/1993 | (WO) . |
| 9428371 | 12/1994 | (WO) . |

OTHER PUBLICATIONS

Windholz et al., *The Merck Index* (1983) p. 1227, ab No. 8388.*

Author Unknown; "1997—A Year in Review, Joint Non Lethal Weapons Program," United States Department of Defense Joint Non–Lethal Weapons Program Website <http://iis.marcorsyscom.usmc.mil/jnlwd/documents/1997jnlwdyearinreview.pdf> (visited Nov. 29, 2000), unknown publication date, internal date Feb. 1998, 21 pages.

Coppernoll, Margaret–Anne, "Ethical and Legal Principles Concerning The Use of Non–Lethal Weapons", National Security Affairs Website <http://nsa.nps.navy.mil./publications/micewski/coppernall.htm> (visited Dec. 5, 2000) unknown publication date, 18 pages.

Coppernoll, Margaret–Anne, "The Nonlethal Weapons Debate", United States Naval War College Website <http://www.nwc.navy.mil/press/Review/1999/spring/art5–SP9.htm> (visited Dec. 5, 2000) unknown publication date; internal copyright date 1998; 14 pages.

Lewer, Nick; "Nonlethal Weapons", Forum For Applied Research and Public Policy Website <http://forum.ra.utk.edu/summer99/nonlethal.htm> (visited Dec. 5, 2000) unknown publication date, 9 pages.

Lewer, Nick et al.; "Non–Lethal Weapons: A Fatal Attraction?"; Zed Books Ltd., 1997; p. 13.

Siniscalchi, Joseph; "Non–Lethal Technologies: Implications For Military Strategy"; Air War College Website <http://www.au.af.mil/au/database/research/ay1997/awc/97–177.htm> (visited Dec. 5, 2000) unknown publication date, internal date Apr. 1997; 75 pages.

Farr et al., "Organic Sulfur Compounds", Patty's Industrial Hygiene and Toxicology, vol. 2, Part F, ppg. 4311–4372, (John Wiley & Sons, Inc., 4th Ed., 1994).

Witten et al., "Malodorous Substances as Riot Control and Troop Training Agents", Edgewood Arsenal Technical Report EATR 4370, Mar. 1970, 30 pages.

Abstract of JP 50014480, 1975, World Patent Index, Section Ch, Week 197525, (Derwent Publications Ltd., 1975).

* cited by examiner

*Primary Examiner*—Kevin E. Weddington
(74) *Attorney, Agent, or Firm*—Sieberth & Patty, L.L.C.

(57) ABSTRACT

The malodorant compositions provided by the invention are formed from ingredients comprised of at least a malodorant compound and a carrier liquid, the compositions having a toxicity category rating of at least III. Preferred malodorant compounds suitable for use in the compositions of this invention of include organic sulfur compounds, and the compositions may include an appropriate amount of an odor intensifier, e.g., skatole, to provide a malodorant composition having low toxicity while providing the olfactory stimuli desired. The combination of these compounds is particularly effective in producing a malodorous stimulus for use in a variety of settings where non-lethal weapons are employed, all without permanently damaging the targeted subject or the surrounding environment. Non-lethal weapon systems for delivering to target the malodorant compositions of this invention, and associated methods of use of the compositions of this invention, are also described.

20 Claims, No Drawings

MALODORANT COMPOSITIONS

REFERENCES TO RELATED APPLICATIONS

This application is a continuation-in-part of application Ser. No. 09/088,334, filed Jun. 1, 1998, now abandoned and incorporated herein by reference, which is a continuation-in-part of application Ser. No.08/937,909, filed Sep. 25, 1997 and incorporated herein by reference, now abandoned.

FIELD OF THE INVENTION

This invention relates to malodorant compositions, weapon systems employing malodorant compositions, and related methods of use.

BACKGROUND

Non-lethal weapon systems represent important force alternatives for law enforcement and strategic defense purposes, and have been investigated for use in a variety of settings. Non-limiting examples of non-lethal weapons that have been developed, or are under development, include tear gases, impact weapons, kinetic energy rounds, flash grenades, acoustic guns, sticky foams, snare nets, stun guns, strobe lights, and other diversionary devices.

In order to ensure the most desirable outcomes in managing low-level conflict, it is desired that numerous choices of non-lethal weapon systems be available along a force continuum, such that a non-lethal weapon suitable for a particular application may be selected based upon the nature of the situation, and on the level of provocation and threat.

Malodorant compositions can be useful as non-lethal weapons or components of non-lethal weapons based on their ability to elicit potent psychological and physiological responses. Without desiring to be bound by theory, it is believed that there are two primary neural components involved in odor detection. One is controlled by the olfactory nerves and is responsible for odor perception and recognition. Olfactory performance is a function of the molecular structure of the odorant, the configuration of odor reception sites within the individual, signal generation at these odor reception sites, and the relative concentration of the odorant. The second odor perception system is controlled by the trigeminal nerve and serves primarily as a warning system against substances that could be potentially harmful.

A variety of responses may be observed upon exposure to malodorant compositions which are believed to stimulate the olfactory and/or trigeminal nerves. These responses may range from immediate nausea, gagging and/or vomiting, to various levels of discomfort. The use of obnoxious olfactory stimuli to control and/or modify human behavior in this way is an attractive concept for modern warfare and low-level conflict management. However, so far as is known, heretofore malodorant compositions have been too toxic for use when seeking to incapacitate and/or disperse an individual, or group of individuals, without causing severe physiological trauma to the body and/or without severely damaging the surrounding environment.

Thus, a need exists for malodorant compositions and alternative, non-lethal weapon systems employing such malodorant compositions to achieve, e.g., behavior modification and/or control, without killing or permanently physically damaging those subject to the physiological effects of the compositions. A need also exists for malodorant compositions which are substantially benign to the surrounding environment. A need further exists for efficient containment vessels and weapon systems which may effectively deliver such malodorant compositions to a target.

SUMMARY OF THE INVENTION

The present invention is deemed to satisfy these and other needs in a highly efficient and effective way. In particular, the malodorant compositions provided by this invention provide an adjutant which meets many of the needs of military forces, law enforcement and security forces in a variety of non-lethal applications, such as crowd/riot control, hostage negotiation, area denial, and other similar situations. The malodorant compositions of this invention may be used as the sole means for a given non-lethal application, or may be employed in combination with other situational tools. The malodorant compositions of this invention offer attractive force alternatives to many conventional weapons systems by providing effective non-lethal options that are substantially less-toxic to both the individual and to the environment as compared with previously known compositions, and that are useful in a variety of settings.

The malodorant compositions of this invention are formulated and delivered under conditions effective to subdue or disperse an individual or group of individuals, while minimizing adverse physiological risk to the individual. The effects typically achieved by use of the malodorant compositions of this invention may include marked nausea, discomfort, and, in some cases, somnolence. In addition, because of their negligible environmental toxicities, the compositions generally do not require post-application environmental decontamination. Thus, the malodorant compositions of this invention are deemed of substantial value to military and civilian agencies whose mission is to stop and/or dissuade riotous or potentially riotous crowds without inflicting lethal force upon the individuals concerned.

In one embodiment of the present invention, a malodorant composition is provided which is comprised of (i.e., formed from ingredients comprising) at least one malodorant compound and a carrier liquid, these components being further defined hereinafter, wherein the composition so formed has a toxicity category rating of at least III. As used in this specification, including the appended claims, "toxicity category rating" means each of dermal irritation, inhalation, dermal sensitization, and eye irritation toxicity category ratings as determined under Proposed Rule, 49 Federal Register 188, in which ratings range from I to IV and None, with I being the most toxic and None being the least. Thus, for example, a composition of this invention has a toxicity category rating of at least III if each of the aforementioned ratings determined in accordance with 49 *Federal Register* 188 is III or higher. The malodorant compound is generally dissolved, diluted or otherwise dispersed in the carrier liquid to form the malodorant composition. Preferably, the composition further comprises at least one odor intensifier, which may be similarly dissolved, diluted or otherwise dispersed in the carrier liquid along with the malodorant compound(s). It may be desired in some instances to include additional components in the malodorant composition, depending on its intended use. These may include, for example, preservatives, marking dyes, ballistic enhancers, anti-foaming agents, anti-static agents, sticking agents, etc.

In accordance with another embodiment of this invention, the malodorant compositions of the present invention may be packaged or otherwise contained in a vessel to allow them to be directed or delivered to an intended target area using any one of a multitude of delivery techniques. Thus, the present invention also provides a device which comprises a containment vessel for storing a liquid material, and within the vessel a liquid material comprised of a malodorant composition formed from ingredients comprising (i) at least one malodorant compound and (ii) a carrier liquid, wherein the malodorant composition so formed has a toxicity category rating of at least III. The containment vessel may be comprised of a "paint ball", grenade, non-lethal land mine, spray bottle, rubber bullet, a modified shotgun shell, or other like vessel. In one preferred embodiment, the containment vessel is a "paint ball" or other non-lethal projectile housing the malodorant composition. Use of such containment vessels enables the malodorant compositions to be beneficially used in a wide range of settings where non-lethal force can be employed to achieve control over the adverse activities of others. For example, the malodorant compositions of the present invention may be used in the peaceful dispersion of unruly crowds, the control of unruly crowd movement, the temporary partial disabling of an unruly individual that is already contained, as an adjutant to hostage negotiation, as an area denial device, as a behavior modifying device, and in other like circumstances.

In yet another aspect of this invention, a method is provided for effecting discomfort in one or more individuals in order to modify the behavior of the individual(s). The method comprises exposing the individual(s) to a malodorant composition formed from ingredients comprising (i) at least one malodorant compound and (ii) a carrier liquid, wherein the malodorant composition so formed has a toxicity category rating of at least III. As used in this disclosure and the appended claims, "exposing" the individual(s) to the malodorant composition means placing the individual(s) in contact with, or in sufficient proximity with, the malodorant composition such that the individual(s) may detect the composition's odor.

In yet another embodiment of this invention, a non-lethal weapon system is provided which comprises a projectable housing containing at least a malodorant composition formed from ingredients comprising at least one malodorant compound and a carrier liquid, wherein the composition has a toxicity category rating of at least III, and wherein the housing may rupture or break upon non-lethal impact with an individual. In another embodiment, the system further comprises a device for projecting the projectile at a non-lethal velocity which is capable of causing the projectile to rupture or break upon non-lethal impact with an individual.

These and other embodiments of this invention will now be appreciated from the following detailed description of specific embodiments of the invention, examples and claims.

DETAILED DESCRIPTION OF SPECIFIC EMBODIMENTS

Illustrative embodiments of the invention are described below. It will of course be appreciated that in the development of any such actual embodiment, numerous implementation-specific decisions must be made in the ordinary course to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

In accordance with the present invention, there are provided malodorant compositions and methods for their use in a variety of situations where lethal force is unnecessary and/or undesired. The compositions typically are formed from ingredients comprising at least two different components, at least one malodorant compound and a carrier fluid. Preferably, the composition is also formed from a third ingredient, an odor intensifier. In all cases, the composition of this invention so formed must have a toxicity category rating of at least III.

The malodorant compound should have sufficient stench characteristics to be effective under the circumstances of intended use. Thus, the malodorant should have immediate strong, repulsive characteristics to achieve desired less-than-lethal purposes of control. The malodorant is preferably comprised of one or more malodorant organic sulfur compounds; organic nitrogen compounds; organic phosphorus compounds; substituted or unsubstituted $C_3$ to $C_6$ aliphatic or cycloaliphatic carboxylic acids, aldehydes or acid halides; aliphatic diynes; inorganic silanes; or the like, including a mixture of two or more of the foregoing. Other suitable candidate malodorant compounds may include, for example, allyl trifluoro acetate; cis-4-decanal; pentafluoropropionic anhydride; 6,6-dimethylfulvene; methyl 4-methylbenzoate; or the like, including a mixture of two or more of the foregoing. As is true for each component of the composition of this invention, in some cases, it may be preferable to use only one compound as the malodorant compound rather than a mixture of two or more compounds, in the event that the combination of compounds may lead to an adverse interaction between compounds, a diminution in the effectiveness of the composition, or an excessive increase in the toxicity of the composition.

Non-limiting examples of potentially suitable organic nitrogen compounds include 1,4-diaminobutane, 1,5-diaminopentane, 4-fluoro-alpha-methylbenzylamine, 2-ethylpyridine, 3-ethylpyridine, 4-ethylpyridine, 2-ethyl-3-methylpyrazine, 3-ethyl-2-methylpyrazine, 2,3-diethylpyrazine, 1-methylpyrrolidine, 1-(dimethylamino)pyrrole, 3-methyl indole, 4-methyl indole, 6-methyl indole, 2,3-diethyl 1-methyl indole, ethyl 1-azetidinepropionate, S-(+)-2-methylbutyronitrile, butyl isocyanide, 1,1,3,3-tetramethylbutyl isocyanide, 1H-benzotriazol-1-ylmethyl isocyanide, isophorone diisocyanate terminated poly (neopentyl glycol adipate), methyl ethyl(tributylstannyl) carbamate, and the like.

Non-limiting examples of potentially suitable organic phosphorus compounds include trimethylphosphine, trimethylphosphine-silver iodide complex, triethylphosphine, tripropylphosphine, dichloroisopropylphosphine, chlorodiisopropylphosphine, dimethylphenylphosphine, ethyldiphenylphosphine, dimethyl phosphite, trimethyl phosphite, dimethyl methylphosphonate, 1,2-bis(dichlorophosphino)ethane, 1,3-dimethyl-2-phenyl-1,3,2-diazaphospholidine, and the like.

Non-limiting examples of potentially suitable substituted or unsubstituted $C_3$ to $C_6$ aliphatic or cycloaliphatic carboxylic acids, aldehydes or acid halides include cyclopropanecarboxylic acid, cyclobutanecarboxylic acid, tert-butylacetic acid, 2-methylbutyric acid, heptafluorobutyric acid, 4-bromobutyric acid, pentafluoropropionic anhydride, butyric anhydride, heptafluorobutyric anhydride, cyclopropanecarboxaldehyde, butyraldehyde, isobutyraldehyde, isovaleraldehyde, 2chloropropionyl chloride, 3- chloropropionyl chloride, 3-phenylpropionyl chloride, valeryl chloride, 2-methylvaleryl chloride, isovaleryl chloride, butyryl chloride, 2-ethylbutyryl chloride, isobutyryl chloride, 4-bromobutyryl chloride, 4-chlorobutyryl chloride, cyclobutanecarbonyl chloride, tert-butylacetyl chloride, allyl trifluoroacetate, and the like.

Non-limiting examples of potentially suitable aliphatic diynes include 1,7-octadiyne, 1,8-nonadiyne, and the like.

Non-limiting examples of potentially suitable inorganic silanes include silane, methylsilane, disilane, silicon tetrachloride, and the like.

Of course, it will be understood that all of the foregoing examples of potentially suitable malodorant compounds may include a mixture of one or more of the foregoing. Moreover, if an organic sulfur compound also includes nitrogen and/or phosphorus, it shall be considered an organic sulfur compound for purposes of this disclosure. Likewise, if an organic phosphorus compound is devoid of sulfur but includes nitrogen, it shall be considered an organic phosphorus compound for purposes of this disclosure.

The malodorant compound more preferably is comprised of one or more organic sulfur compounds. The organic component of the organic sulfur compounds may be comprised of one or more linear, non-linear, and/or cyclic arrangement of carbon atoms, and may contain saturated and/or unsaturated carbon bonding. Moreover, the organic component of the organic sulfur compound may contain non-carbon atoms and/or chemical functionalities, as desired. The organic sulfur compounds useful in forming the compositions of this invention may include essentially any malodorous sulfur containing compound which further comprises an organic component.

Illustrative, non-limiting examples of organic sulfur compounds useful in this invention include generally organic mercaptans, organic thiols, organic sulfides, organic disulfides, organic sulfoxides, organic sulfones, organic sulfonic acids, organic sulfinic acids, organic thio-acids, organic dithio-acids, organic thiolo-acids, organic thiono-acids, organic sulfonyl halides, organic thiazoles, organic sulfur amines, and the like, including mixtures of any two or more of the foregoing. Suitable non-limiting examples of such compounds include methyl mercaptans, ethyl mercaptans, propyl mercaptans, butyl mercaptans, amyl mercaptans, phenyl mercaptans, benzyl mercaptans, 2-mercaptoethanol, 1,2-ethanedithiol, 3-methyl-1-butanethiol, ethylcyclohexydithiol, d-limonene dimercaptan, vinyl cyclohexene-derived dimercaptan, perchloromethyl mercaptan, methyl sulfide, ethyl sulfide, propyl sulfide, isopropyl sulfide, ethyl methyl sulfide, dimethyl sulfide, dimethyl disulfide, diethyl sulfide, di-n-propyl disulfide, butyl disulfide, bibutyl sulfide, trimethylene sulfide, ethylene sulfide, propylene sulfide, allyl sulfide, mercaptoethyl sulfide, cyclopropyl phenyl sulfide, dimethyl trisulfide, dimethyl sulfoxide, propyl allyl sulfoxide, 3-chloropropyl n-octyl sulfoxide, allyl n-octyl sulfoxide, 2-methallyl n-octyl sulfoxide, methanesulfonic acid, methanesulfonyl chloride, ethanesulfonyl chloride, propanesulfonyl chloride, benzothiazole, 2-mercaptobenthiazole, N-isopropyl-2-benzothiazolesulfenamide, N,N-diisopropyl-2-benzothiazolesulfenamide, N-tert-butyl-2-benzthizolesulfenamide, N-cyclohexyl-2-benzothiazolesulfenamide, N,N-dicyclohexylbenzothiazolesulfenamide, and other like malodorous organic sulfur compounds, including mixtures of any two or more of the foregoing.

In a preferred embodiment of this invention, the organic sulfur compounds used in the malodorant compositions of the present invention comprise aliphatic mercaptans, and other structurally related compounds, wherein the aliphatic component of the mercaptan comprises about 3 to about 12 carbon atoms per molecule. Examples of such compounds include methyl mercaptans, ethyl mercaptans, propyl mercaptans, isopropyl mercaptans, -butyl mercaptans, isobutyl mercaptans, s-butyl mercaptans, t-butyl mercaptans, -amyl mercaptans, s-amyl mercaptans, isoamyl mercaptans, t-amyl mercaptans, n-hexyl mercaptans, n-heptyl mercaptans, n-octyl mercaptans, s-octyl mercaptans, n-nonyl mercaptans, t-nonyl mercaptans, n-decyl mercaptans, undecyl mercaptans, n-dodecyl mercaptans, t-dodecyl mercaptans, triisobutyl mercaptans, and the like, including mixtures of any two or more of the foregoing. More preferred are the aliphatic organic sulfur compounds having either 4 or 12 carbon atoms, e.g., n-, t- or iso-butyl mercaptans or n-, t- or triisobutyl mercaptans, or a mixture thereof, with n-, t- or iso-butyl mercaptans being particularly preferred because of their combination of relatively low toxicity and powerful stench.

The concentration of the malodorant compound or compounds in the malodorant compositions of the invention may vary depending on the particular malodorant compound employed, and on the application for which the malodorant composition is intended, with the proviso that the concentration employed may not be such so as to decrease the toxicity category rating of the composition below III. When the malodorant compound comprises an organic sulfur compound, the malodorant compound is typically present in the malodorant composition at a concentration in the range of about 10 wt. % to about 90 wt. %, and more preferably in the range of about 50 wt. % to about 80 wt. %, based upon the weight of the malordorant composition.

In addition to the malodorant compound, the malodorant compositions of the present invention may further comprise a component which is an odor intensifier such as, for example, skatole. Skatole is an indole which is a component of fecal matter, and is commonly used in perfumes at very low concentrations for its odor intensifying properties. The term "skatole" typically refers to the compound, 3-methylindole, which has the following structural formula:

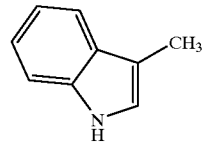

The odor intensifiers of this invention should be different from the malodorant compound and are those which potentiate the odor characteristics of the malodorant compound(s) with which they are employed. For example, indoles serving as a candidate odor-intensifiers of this invention may include 3-methyl indole, 4-methyl indole, 6-methyl indole 2,3-diethyl 1-methyl indole, and the like including mixtures of any two or more of the foregoing. Skatole is preferred because of its ability at low concentrations to potentiate the odor of the malodorant compound without substantially contributing toxicity to the overall composition. However, other odor intensifiers may be used. The best way of establishing the suitability of such candidate odor intensifiers for use pursuant to this invention is to perform a few simple preliminary tests. Such tests involve utilizing non-toxic amounts of a selected malodorant compound and a candidate odor intensifier in the proportions described herein, and comparing malodorant characteristics of such compositions to the malodorant characteristics of an identical composition which is devoid of the candidate odor intensifier. Such a determination is best made by utilizing a panel of individuals having the ability of distinguishing readily the malodorant characteristics and intensities of different compositions. Use of panels in this manner is well known in the art of fragrance and malodorant compositions. See, e.g., U.S. Pat. No. 4,487,613.

The intensity and lasting effect of the malodor may be controlled by the concentration of odor intensifier present in the malodorant composition. The odor intensifier and the concentration thereof should chosen such that the malodorant composition formed has a toxicity category rating of at least III. When the odor intensifier is skatole, the concentration of odor intensifier desired may vary for a given application, but it will be preferably in the range of about 0.05 wt. % to about 5 wt. %, and more preferably in the range of about 0.5 wt. % to about 1.5 wt. %, based upon the weight of the malodorant composition. In this way, the desired odor intensifying effect may be achieved while also minimizing composition toxicity to achieve a toxicity category rating of at least III, and more preferably of at least IV.

The malodorant compound, and when present the odor intensifier, may be dissolved, diluted, or otherwise dispersed, in a carrier liquid which may be an aqueous, organic, and/or oil-based carrier or diluent liquid. This carrier liquid may be comprised of any one or more of a variety of compounds, and its selection may vary depending on the particular malodorant compound used and on the application for which the malodorant composition is intended. Examples of suitable diluents may include water or water-based solutions and buffers, organic solvents (e.g., esters, ethers, ketones, nitriles, hydrocarbons, etc.), and oleaginous liquids, both natural and synthetic, including mixtures of any two or more of the foregoing. Non-limiting examples of suitable oleaginous liquids include mineral oils; natural oils such as castor oil, cottonseed oil, olive oil, almond oil, peanut oil, rapeseed oil, corn oil, sesame oil, safflower oil, hemp oil, linseed oil, tung oil, oiticica oil, jojoba oil, meadowfoam oil, and the like. Other suitable oleaginous liquids may include synthetic oils such as homo- and inter-polymers of $C_2$–$C_{12}$ olefins, carboxylic acid esters of both monoalcohols and polyols, polyethers, silcones, polyglycols, silicates, alkylated aromatics, carbonates, thiocarbonates, orthoformates, phosphates and phosphites, borates and halogenated hydrocarbons. Representative of such oils or homo- and interpolymers of $C_2$–$C_{12}$ monoolefinic hydrocarbons, alkylated benzenes (e.g., dodecyl benzenes, didodecyl benzenes, tetradecyl, benzenes, dinonyl benzenes, di-(2-ethylhexyl-)benzenes, wax-alkylated naphthalenes); and polyphenyls (e.g., biphenyls, terphenyls). Alkylene oxide polymers and interpolymers and derivatives thereof where the terminal hydroxyl groups have been modified by esterification, etherfication, etc., constitute another class of synthetic oils. These are exemplified by the oils prepared through polymerization of alkylene oxides such as ethylene oxide or propylene oxide, and the alkyl and aryl ethers of these polyoxyalkylene polymers (e.g., methyl polyisopropylene glycol ether having an average molecular weight of 1,000, diphenyl ether of polyethylene glycol having a molecular weight of 500–1,000, diethyl ether of polypropylene glycol having a molecular weight of 1,000–1,500) or mono- and poly-carboxylic esters thereof, for example, the acetic acid ester, mixed $C_3$–$C_6$ fatty acid esters, or the $C_{13}$ Oxo acid diester of tetraethylene glycol.

Another suitable class of synthetic oils comprises the esters of dicarboxylic acids (e.g., phthalic acid, succinic acid, maleic acid, azelaic acid, suberic acid, sebacic acid, fumaric acid, adipic acid, linoleic acid dimer) with a variety of alcohols (e.g., butyl alcohol, hexyl alcohol, dodecyl alcohol, 2-ethylhexyl alcohol, and ethylene glycol). Specific examples of these esters include dibutyl adipate, di(2-ethylhexyl) adipic, didodecyl adipate, di(tridecyl) adipate, di(2-ethylhexyl) sebacate, dilauryl sebacate, di-n-hexyl fumarate, dioctyl sebacate, diisooctyl azelate, diisodecyl azelate, dioctyl phthalate, didecyl phthalate, di(eicosyl) sebacate, the 2-ethylhexyl diester of linoleic acid dimer, and the complex ester form by reacting one mole of sebacic acid with two moles of tetraethylene glycol and two moles of 2-ethylhexanoic acid.

Potentially suitable silicon-based oils such as the polyalkyl-, polyaryl-, polyalkoxy-, or polyaryloxy-siloxane oils and silicate oils comprise another class of synthetic compounds (e.g., tetraethyl silicate, tetraisopropyl silicate, tetra-(2-ethylhexyl) silicate, tetra-(p-tert-butylphenyl) silicate, poly(methyl)siloxanes, and poly(methylphenyl) siloxanes). Other suitable synthetic oils may include liquid esters of phosphorus-containing acids (e.g., tricresyl phosphate, trioctyl phosphate, triphenyl phosphite, and diethyl ester of decane phosphonic acid.

Other esters which may be used as a carrier liquid include, for example, those made from $C_3$–$C_{18}$ monocarboxylic acid and polyols and polyol ethers such as neopentyl glycol, trimethylolpropane, pentaerythritol and dipentaerythritol tetracaproate, the ester formed from trimethylolpropane, caprylic acid and sebacic acid, and the polyesters derived from a $C_4$–$C_{14}$ dicarboxylic acid and one or more aliphatic dihydric $C_3$–$C_{12}$ alcohols such as derived from azelaic acid or sebacic acid and 2,2,4-trimethyl-1,6-hexanediol serves as examples. Also useful as the carrier liquid are hydrogenated or unhydrogenated liquid oligomers $C_6$–$C_{16}$ α-olefins. Preferably, the carrier liquid is one which effectively lowers the volatility of the malodorant composition as compared to the composition which is substantially devoid of the carrier liquid. In one preferred embodiment, a plant oil is used to improve physical characteristics such as, e.g., improve viscosity, lower volatility, etc., and to facilitate storage and/or transportation. In any event, it will now be appreciated that the composition which includes the carrier liquid should always have a toxicity category rating of at least III.

Depending on the particular application and/or method for delivering the malodorant composition to its intended target area, it may be desirable to include other chemical components in the compositions. These may include preservatives, such as ethylene diamine tetraacetic acid (EDTA), marking dyes (e.g., permanent, non-permanent, fluorescent, or iridescent dyes, etc.), viscosity modifiers, bismuth and other like compounds for enhancing ballistic properties, anti-foaming agents, anti-static agents, and the like, including mixtures of any two or more of the foregoing.

Again without being bound to theory, it is believed that the malodorant compositions of this invention deliver a stimulus that is perceived by the olfactory and/or trigeminal nerves. The response is typically characterized by a strong desire to avoid the substance and may be, and often is accompanied by immediate nausea and gagging. Persons exposed to the malodor will be naturally averse to the substance and will generally clear an area in which the composition has been dispersed, thus lowering the potential for conflict. The residue of the compositions may be removed with a non-toxic formulation and is not detrimental to the environment in typical quantities used for crowd control and other non-lethal applications.

In practicing the method of this invention for effecting discomfort in one or more individuals in order to modify the behavior of the individual(s). The individual(s) are exposed to a malodorant composition of this invention. Such exposure may be accomplished in a wide variety of ways. For example, the malodorant composition can be delivered to an intended target (individual(s) or a place) by any one of a variety of means, including spray delivery, air drop, and triggered explosive dispersion or projectile delivery to a target using a containment vessel or a projectable housing. When used, suitable containment vessels may include, e.g., bottles, "paint balls", grenades, non-lethal land mines, rubber bullets, modified shotgun shells, modified arrows, and the like, with the proviso that when using containment vessels for storing or delivering the malordorant, the vessel preferably is fabricated from or lined with a material which is substantially inert when placed in contact with the mal-ordorant composition. The effective range for crowd control and other applications is limited only by the user's selection among these and other suitable approaches. By selection of an appropriate delivery means, it is envisioned that the malodorant compositions will be beneficial in a wide range of applications, e.g., for peaceful dispersion of unruly crowds or mobs, for incapacitation of instigators or other key personnel, for denial and or discouragement of access to specific areas, for peaceful clearing of personnel from structures and facilities, for control of movement of crowds, for neutralization of vehicles, aircraft, vessels, and facilities, as an adjutant in hostage negotiations, an alternative to anti-personnel land mines, as a first line warning device to civilian personnel not to enter an area, and other like scenarios.

In the non-lethal weapon system of this invention, the projectable housing which contains at least the malodorant composition of this invention should be such that it may rupture or break upon non-lethal impact with an individual. Suitable non-limiting examples of suitable projectable housings include modified shotgun shells, rubber bullets, "paint balls" and the like. In one preferred embodiment of the weapon system of this invention, the malodorant composition is contained within a projectable housing in the form of a "paint ball" (for example, using a "paint ball" as described in either of U.S. Pat. Nos. 5,001,880 or 5,254,379, which are hereby incorporated by reference in their entirety). A so-called "heavy" (0.68 gm) paintball is particularly preferred for enhanced ballistic characteristics. The projectable housings may be comprised of essentially any class of material provided the material is capable of remaining intact during projection to the target and releasing its contents at an effective point in time, and that the projectable housing material which is in contact with the malodorous composition does not adversely react with the composition in a manner which compromises the desired potency of the malodor or the integrity of the material. Such projectable housings may be made from or lined with, for example, a frangible glass or glass-like material, polymeric materials such as polystyrene, Teflon®, and the like. While stainless steel material may also be used to fabricate the projectable housings, such material is less preferred when the vessel is designed to impact against or near the body of a human target and may produce hazardous projectile fragments.

In order to deliver the malodorant composition to the intended target area, the projectable housing in the weapon system of this invention will generally be projected toward a target by a device capable of projecting the projectile housing at a non-lethal velocity which velocity is capable of causing the projectile to rupture or break upon non-lethal impact with an individual. Non-limiting examples of suitable devices include modified bows, sling shots, cannons, guns, air guns, etc. In a preferred embodiment of the invention, the device for projecting the housing is a device capable of delivering the housing as a projectile to a target area with a high degree of precision using an air or similarly powered gun or gunlike apparatus. One example of such a device is marketed under the name Underbarrel Tactical Paintball System (UTPBS), by Monterey Bay Corporation, Columbia, Md. The UTPBS is a pneumatic "paint ball" gun that may be mounted securely under the barrel of, for example, a standard M-16A2 weapon, occupying approximately the same volume as the Army standard M-103 40 mm grenade launcher and using the same mounting points for secure attachment to the weapon. Depending upon the size and weight of the projectile, the effective range of the UTPBS can be approximately 100 meters, providing the user with a true "stand off" non-lethal capability.

In another exemplary embodiment of this invention, the malodorant compositions are used in combination with a containment vessel as an alternative to explosive land mines. Land mines have been in use for centuries. During the $20^{th}$ century in particular, land mines have been extensively used world-wide to deny areas of ground, to canalize expected enemy attack, and to cause casualties to the enemy. Explosive mines and booby traps are an inexpensive means for hindering enemy movements. However, they have also caused great suffering and misery to many innocent civilians around the world. Indiscriminate use of explosive mines by rebels and government troops alike has rendered large areas of land unsafe for human activity. While recent treaties have made the first steps in outlawing explosive land mines, there remains a valid need for effective security approaches in order to protect areas with minimal human and financial cost. To meet this need, it is envisioned that the compositions of this invention will be beneficial in the production and use of malodorant land mines, in which the composition is released from a mine upon activation. By proper design of an appropriate mine apparatus, this may be achieved relatively inexpensively, would not require clearing of the mines after use, and would eliminate the danger of unintentional loss of life.

The following examples are provided to demonstrate certain illustrative embodiments of this invention. It should be appreciated by those skilled in the art that the techniques disclosed in the examples which follow represent those found by the inventors to function in the practice of the invention. However, those skilled in the art should, in light of the present disclosure, appreciate that many changes can be made in the specific embodiments which are disclosed herein and still obtain a like or similar result without departing from the spirit and scope of the invention.

EXAMPLE 1

A malodorant composition was prepared at ambient temperature without the manipulation of temperature, under ambient atmosphere and at atmospheric pressure, according to the following formulation:

| | |
|---|---|
| n-butyl mercaptan | 750 ml |
| 3-methylindole | 10 g |
| t-butyl mercaptan | 50 ml |
| cottonseed oil | 200 ml |

This illustrative composition is able to a withstand temperature changes in its containment vessels between −20 degrees F. to 125 degrees F. It is comprised of alkyl mercaptans having minimal toxicity characteristics and low thresholds of perception. Toxicological studies of the composition were conducted in accordance with EPA Pesticide Assessment Guidelines, Subdivision F, Hazard Evaluation: Human and Domestic Animals, Series 81-1 and OPPTS 870.1100 (for acute oral toxicity potential), Series 81-2 and OPPTS No. 870.1200 (for acute dermal toxicity potential) Series 81-3 and OPPTS No. 870.1300 (for inhalation toxicity potential), Series 81-4 and OPPTS No. 870.2400 (for eye irritation potential), and Series 81-5 and OPPTS No. 870.2500 (for dermal irritation potential). In addition, sensitizing potential was determined using a modification of the Buehler method (Rithz, H. L. and E. V. Buehler, "Planning, Conduct, and Interpretation of Guinea Pig Sensitization Patch Tests," Concepts in Cutaneous Toxicity, p. 28, Academic Press, NY, 1980) in accordance with EPA Pesticide Assessment Guidelines, Subdivision F, Hazard Evaluation: Human and Domestic Animals, Series 81-6 and OPPTS No. 870.2600. The results of the studies are summarized in the following Table 1.

TABLE 1

| Acute Toxicity | Example 1 Composition |
| --- | --- |
| Inhalation $LD_{50}$ (mg/m$^3$; rat) | >5950 |
| Dermal $LD_{50}$ (mg/kg; rabbit) | >5050 |
| Oral $LD_{50}$ (mg/kg; rat) | 1935–2083 |
| Skin Irritation | Slight |
| Eye Irritation | Slight |
| Skin Sensitization | None |

As used in the foregoing Table 1, "$LD_{50}$" represents the dose level which is lethal for 50% of the test population. The composition was assessed for toxicity category rating in accordance with
49 *Federal Register* 188, and the ratings were as follows:
Rabbit Dermal Toxicity: Category IV
Rat Inhalation Toxicity: Category IV
Rabbit Dermal Irritation: Category IV
Guinea Pig Skin Sensitization: Category IV

EXAMPLE 2

Another illustrative malodorant composition is prepared under a nitrogen blanket at a pressure of 2 psig without manipulation of temperature, according to the following formulation:

| n-butyl mercaptan | 750 ml |
| --- | --- |
| 3-methylindole | 10 g |
| mercaptoethyl sulfide | 10 g |
| 3-methyl-1-butanethiol | 10 g |
| cottonseed oil | 220 ml |

Because some individuals lack sensitivity to certain odors, i.e., are asnomic (approximately 1 in 500), a composition according to the above formulation contains multiple malodorous organic sulfur compounds in order to minimize the possibility that an individual may be insufficiently affected by the composition.

EXAMPLE 3

Yet another illustrative malodorant composition is prepared under nitrogen blanket at a pressure of 2 psig without manipulation of temperature, according to the following formulation:

| 2-mercaptoethanol | 800 ml |
| --- | --- |
| 3-methylindole | 10 g |
| distilled water | 190 ml |

This illustrative composition is water-soluble and has a relatively high volatility. Thus, it may be desirable for use in situations where the malodor needs to be cleared within a shorter duration of time than those using an oil-based carrier.

The malodorant compositions of this invention may be made using continuous, semi-continuous, or batch processes. While ambient atmosphere, temperature and pressure may be used, preferably the composition is formed under an inert atmosphere (e.g., nitrogen, argon, etc.) at temperatures and pressures which enable the efficient handling of ingredients and formed composition under the particular circumstances, depending upon the application in which the composition will be employed.

It is to be understood that the reactants and/or components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and/or components are identified as ingredients to be brought together in connection with performing a desired chemical reaction or in forming a mixture to be used in accordance with this disclosure. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that the substance, component or ingredient may have lost its original identity through a chemical reaction or transformation during the course of such contacting, blending or mixing operations is thus wholly immaterial for an accurate understanding and appreciation of this disclosure and the claims thereof.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A malodorant composition formed from ingredients consisting essentially of (i) at least one malodorant organic sulfur compound, (ii) a carrier fluid, and (iii) at least one odor intensifier, wherein the composition so formed has a toxicity category rating of at least III.

2. The malodorant composition of claim 1, wherein the odor intensifier comprises skatole.

3. The malodorant composition of claim 2, wherein the amount of skatole used to form the malodorant composition is in the range of about 0.05 wt. % to about 5 wt. %, based upon the weight of the malodorant composition.

4. The malodorant composition of claim 3, wherein the amount of skatole used to form the malodorant composition is in the range of about 0.5 wt. % to about 1.5 wt. %, based upon the weight of the malodorant composition.

5. The malodorant composition of claim 4, wherein the malodorant organic sulfur compound comprises an aliphatic mercaptan containing in the range of about 3 to about 12 carbon atoms per molecule.

6. The malodorant composition of claim 5, wherein the aliphatic mercaptan is selected from the group consisting of methyl mercaptan, ethyl mercaptan, propyl mercaptan, isopropyl mercaptan, -butyl mercaptan, isobutyl mercaptan, s-butyl mercaptan, t-butyl mercaptan, -amyl mercaptan, s-amyl mercaptan, isoamyl mercaptan, t-amyl mercaptan, n-hexyl mercaptan, n-heptyl mercaptan, n-octyl mercaptan, s-octyl mercaptan, n-nonyl mercaptan, t-nonyl mercaptan, n-decyl mercaptan, undecyl mercaptan, n-dodecyl mercaptan, t-dodecyl mercaptan, triisobutyl mercaptan, and a mixture of any two or more of the foregoing.

7. The malodorant composition of claim 6, wherein the aliphatic mercaptan is selected from the group consisting of n-butyl mercaptan, isobutyl mercaptan, s-butyl mercaptan, t-butyl mercaptan, n-dodecyl mercaptan, t-dodecyl mercaptan, triisobutyl mercaptan, and a mixture of any two or more of the foregoing.

8. The malodorant composition of claim 7, wherein the odor intensifier comprises skatole.

9. The malodorant composition of claim 8, wherein the amount of skatole used to form the malodorant composition is in the range of about 0.05 wt. % to about 5 wt. %, based upon the weight of the malodorant composition.

10. The malodorant composition of claim 9, wherein the amount of skatole used to form the malodorant composition is in the range of about 0.5 wt. % to about 1.5 wt. %, based upon the weight of the malodorant composition.

11. The malodorant composition of claim 10, wherein the malodorant organic sulfur compound is selected from the group consisting of n-butyl mercaptan, isobutyl mercaptan, s-butyl mercaptan, t-butyl mercaptan, and a mixture of any two or more of the foregoing.

12. The malodorant composition of claim 11, wherein the carrier fluid comprises a plant oil.

13. The malodorant composition of claim 1, wherein the carrier fluid comprises a plant oil.

14. The malodorant composition of claim 11, wherein the malodorant organic sulfur compound is n-butyl mercaptan.

15. The malodorant composition of claim 14, wherein the carrier fluid comprises a plant oil.

16. The malodorant composition of claim 11, wherein the malodorant organic sulfur compound is a mixture of n-butyl mercaptan and t-butyl mercaptan.

17. The malodorant composition of claim 16, wherein the carrier fluid comprises a plant oil.

18. The malodorant composition of claim 11 wherein the malodorant organic sulfur compound is a mixture of n-butyl mercaptan, mercaptoethyl sulfide and 3-methyl-1-butanethiol.

19. The malodorant composition of claim 18, wherein the carrier fluid comprises a plant oil.

20. The malodorant composition of claim 1 wherein the malodorant organic sulfur compound is 2-mercaptoethanol, the carrier fluid is water, and the odor intensifier is 3-methylindole.

* * * * *